(12) United States Patent
Frederick et al.

(10) Patent No.: US 7,160,332 B2
(45) Date of Patent: Jan. 9, 2007

(54) LINE ASSEMBLY FOR PROSTHETIC COMPONENTS

(75) Inventors: Phil Frederick, Memphis, TN (US); Jeff Shea, Memphis, TN (US); Brian McKinnon, Bartlett, TN (US); David Kelman, Collierville, TN (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 11/176,656

(22) Filed: Jul. 7, 2005

(65) Prior Publication Data

US 2005/0246031 A1    Nov. 3, 2005

Related U.S. Application Data

(62) Division of application No. 10/113,095, filed on Apr. 1, 2002, now Pat. No. 6,916,342.

(51) Int. Cl.
*A61F 2/32* (2006.01)
(52) U.S. Cl. ................................. 623/22.29
(58) Field of Classification Search .. 623/22.15–22.21, 623/22.24, 22.25, 22.28, 22.29; 606/81
See application file for complete search history.

(56) References Cited

U.S. PATENT DOCUMENTS

| | | |
|---|---|---|
| 3,656,184 A | 4/1972 | Chambers |
| 3,894,297 A | 7/1975 | Mittelmeier et al. |
| 4,241,463 A | 12/1980 | Khovaylo |
| 4,279,041 A | 7/1981 | Buchholz |
| 4,619,658 A | 10/1986 | Pappas et al. |
| 4,624,674 A | 11/1986 | Pappas et al. |
| 4,676,798 A | 6/1987 | Noiles |
| 4,678,472 A | 7/1987 | Noiles |
| 4,770,658 A | 9/1988 | Geremakis |
| 4,798,610 A | 1/1989 | Averill et al. |
| 4,908,033 A | 3/1990 | Frey et al. |
| 4,919,674 A | 4/1990 | Schelhas |
| 4,936,855 A | 6/1990 | Sherman |
| 4,950,299 A | 8/1990 | Noiles |
| 4,960,427 A | 10/1990 | Noiles |
| 5,002,577 A | 3/1991 | Bolesky et al. |

(Continued)

FOREIGN PATENT DOCUMENTS

CH    644 511 A    8/1984

(Continued)

OTHER PUBLICATIONS

T. Cobb, et al., *The Elevated-Rim Acetabular Liner in Total Hip Arthroplasty: Relationship to Postoperative dislocation*, Journal of Bone and Joint Surgery, vol. 78-A, No. 1, Jan. 1996, pp. 80-86.

(Continued)

*Primary Examiner*—Eduardo C. Robert
*Assistant Examiner*—Michael J. Araj
(74) *Attorney, Agent, or Firm*—Kilpatrick Stockton LLP (57) ABSTRACT

Methods, systems and devices related to prosthetic implants, including a device for preventing prosthetic components from separating from each other, and more specifically to an assembly for adapting a prosthetic component to receive a device for preventing an implant stem head from dislocating from a prosthetic component. Methods, systems and devices according to this invention seek to provide improved orthopedic prosthetic components and more specifically, improved constrained components that may be utilized with existing implanted prosthetic components. Liner assemblies and systems according to various embodiments of this invention may include an adapter component designed to link current prosthetic cup geometry to a constrained liner, while providing optimal range of motion and sufficient lever out.

21 Claims, 11 Drawing Sheets

U.S. PATENT DOCUMENTS

| | | | |
|---|---|---|---|
| 5,019,105 A | 5/1991 | Wiley | |
| 5,049,158 A | 9/1991 | Engelhardt et al. | |
| 5,062,853 A | 11/1991 | Forte | |
| 5,133,763 A | 7/1992 | Mullers | |
| 5,226,917 A | 7/1993 | Schryver | |
| 5,263,988 A | 11/1993 | Huebner | |
| 5,310,408 A | 5/1994 | Schryver et al. | |
| 5,314,487 A | 5/1994 | Schryver et al. | |
| 5,314,491 A * | 5/1994 | Thongpreda et al. | 623/22.29 |
| 5,358,532 A | 10/1994 | Evans et al. | |
| 5,383,938 A | 1/1995 | Rohr et al. | |
| 5,425,778 A | 6/1995 | Zichner et al. | |
| 5,458,649 A | 10/1995 | Spotorno et al. | |
| 5,507,826 A | 4/1996 | Besselink et al. | |
| 5,549,681 A | 8/1996 | Segmuller et al. | |
| 5,549,693 A | 8/1996 | Roux et al. | |
| 5,658,348 A * | 8/1997 | Rohr, Jr. | 623/22.29 |
| 5,676,704 A | 10/1997 | Ries et al. | |
| 5,725,587 A | 3/1998 | Garber | |
| 5,725,591 A | 3/1998 | DeCarlo, Jr. et al. | |
| 5,782,928 A | 7/1998 | Ries et al. | |
| 5,800,555 A * | 9/1998 | Gray, III | 623/22.29 |
| 5,824,108 A | 10/1998 | Huebner | |
| 5,879,404 A | 3/1999 | Bateman et al. | |
| 5,916,270 A | 6/1999 | Lipman | |
| 5,931,870 A | 8/1999 | Cuckler et al. | |
| 5,935,175 A | 8/1999 | Ostiguy, Jr. et al. | |
| 5,964,809 A | 10/1999 | Lin et al. | |
| 5,989,293 A | 11/1999 | Cook et al. | |
| 5,989,294 A * | 11/1999 | Marlow | 623/22.16 |
| 6,042,611 A | 3/2000 | Noiles | |
| 6,042,612 A | 3/2000 | Voydeville | |
| 6,093,208 A | 7/2000 | Tian | |
| 6,096,083 A | 8/2000 | Keller et al. | |
| 6,099,571 A | 8/2000 | Knapp | |
| 6,129,765 A | 10/2000 | Lopez et al. | |
| 6,206,929 B1 | 3/2001 | Ochoa et al. | |
| 6,248,132 B1 * | 6/2001 | Harris | 623/22.15 |
| 6,249,132 B1 | 6/2001 | Amemiya | |
| 6,475,243 B1 | 11/2002 | Sheldon et al. | |
| 6,916,342 B1 | 7/2005 | Frederick et al. | |
| 2005/0071015 A1 | 3/2005 | Sekel | |
| 2005/0240276 A1 | 10/2005 | Shea et al. | |

FOREIGN PATENT DOCUMENTS

| | | |
|---|---|---|
| DE | 32 15 583 A1 | 12/1982 |
| DE | 93 12 150 U | 10/1993 |
| DE | 199 04 436 A1 | 8/2000 |
| DE | 200 11 728 U | 11/2000 |
| DE | 199 26 923 A | 12/2000 |
| EP | 0 412 438 A | 2/1991 |
| EP | 0 611 008 A | 8/1994 |
| EP | 0 694 294 A1 | 7/1995 |
| EP | 0 694 294 A | 1/1996 |
| EP | 0 773 007 B1 | 5/1997 |
| EP | 0 867 158 A | 9/1998 |
| EP | 0 945 109 A | 9/1999 |
| FR | 2 430 221 A | 2/1980 |
| FR | 2 437 199 A | 4/1980 |
| FR | 2 684 544 | 6/1993 |
| FR | 2 684 544 A | 6/1993 |
| FR | 2 765 100 A | 12/1998 |
| FR | 2 785 524 A | 5/2000 |
| FR | 2 785 525 A | 5/2000 |
| FR | 2 795 302 A | 12/2000 |
| WO | WO 94/05234 | 3/1994 |
| WO | WO 95/22944 | 8/1995 |
| WO | WO 01/76511 A | 10/2001 |
| WO | WO 02/00141 A | 1/2002 |
| WO | WO 02/087476 A1 | 11/2002 |
| WO | WO 005/087141 | 9/2005 |

OTHER PUBLICATIONS

CeraNews Special DUOLOX®-System aus BIOLOX® forte, Feb. 1998, four pages.

Anderson, et al. "Constrained Acetabular Components," *The Journal of Arthroplasty*, 9(1):17-23 (1994).

Lombardi, et al., "Preliminary Report on the S-ROM™ Constraining Acetabular Insert: A Retrospective Clinical Experience," *Orthopedics*, 14(3):297-303 (1991).

Brochure entitled "Howmedica Osteonics Constrained Acetabular Insert Surgical Protocol," *Stryker Howmedica Osteoncs*, 11 pages. (1999).

Brochure entitled Ringloc® Constrained Liner Technique, *Biomet Inc.*, 6 pages (1998).

Tradonsky, et al., "A comparsion of the Disassociation Strength of Modular Acetabular Components," *Clinical Orthopaedics and Related Research*, 296:154-160 (1993).

Rosner, et al., Cup-Liner Conformity of Modular Acetabular Designs, Orthopaedic Research Laboratories, The Mt. Sinai Medical Center, Cleveland, Ohio 44106, six pages (1995).

Goetz, et al., "Salvage of Total Hip Instability with a Constrained Acetabular Component," *Clinical Orthopaedics and Related Research*, 355:171-181 (1998).

Goetz, et al., "Salvage of a Recurrently Dislocating Total Hip Prosthesis with Use of a Constrained Acetabular Component. A Retropective Analysis of Fifty-Six Cases," *Journal of Bone and Joint Surgery*, 80-A(4):502-509 (1998).

Cameron, H., "Use of a Constrained Acetabular Component in Revision Hip Surgery." *Contemporary Orthop.*, 23(5):481-484 (1991).

Fisher, et al., "Constrained Acetabular Cup Disassembly," *Journal Arthrop.*, 9(3):325-329 (1994).

Kaper, B., P. et al., "Failure of a Constrained Acetabular Prosthesis of a Total Hip Arthroplasty," *Journal of Bone and Joint Surgery*, 80-A(4):561-565 (1998).

Schulte, et al., "The outcome of Charnley total hip arthroplasty with cement after a minimum twenty-year followup. The results of one surgeon," *Journal of Bone and Joint Surgery*, 75-A(7):961-975 (1993).

Turner, "Postoperative Total Hip Prosthetic Femoral Head Dislocations. Incidence, Etiologic Factors, and Management," *Clinical Orthopaedics and Related Research*, 301:196-204 (1994).

Paterno, et al., "The influence of patient related factors and the position of the acetabular component on the rate of dislocation after total hip replacement," *Journal of Bone and Joint Surgery*, 79A(8) (1997).

Ali Khan, et al., "Dislocation Following Total Hip Replacement," *Journal of Bone and Joint Surgery*, 214-218 (1981).

Hedlundh, et al., "Influence of Surgical Approach on Dislocations After Charnley Hip Arthroplasty," *Journal of Arthroplasty*, 10(5):609-614 (1995).

Kristiansen, et al., "Dislocation Following Total Hip Arthroplasty," *Arch. Orthop. Trauma Surg.*, 103:375-377 (1985).

Morrey, "Difficult Complications After Hip Joint Replacement Dislocation," *Clinical Orthopaedics and Related Research*, 344:179-187 (1997).

Woo, et al., "Dislocations after Total Hip Arthroplasty," *Journal of Bone and Joint Surgery*, 64-A(9):1295-1306 (1982).

\* cited by examiner

LINE ASSEMBLY FOR PROSTHETIC COMPONENTS

CROSS REFERENCE TO RELATED APPLICATION

This application is a divisional of U.S. patent application Ser. No. 10/113,095 entitled "Liner Assembly for Prosthetic Components," filed on Apr. 1, 2002 now U.S. Pat No. 6,916,342, now allowed, the contents of which are incorporated herein by reference.

FIELD OF THE INVENTION

The invention is directed generally to methods, systems and devices related to prosthetic implants, including devices for preventing prosthetic components from separating from each other, and more specifically to assemblies for adapting a prosthetic component to receive a device for retaining or preventing an implant stem head from dislocating from a prosthetic component.

BACKGROUND

Artificial implants, including hip joints, shoulder joints and knee joints, are widely used in orthopedic surgery. Artificial hip joints are generally ball and/or socket joints, designed to match as closely as possible the function of the natural joint. The ball and socket joint of the human hip connects the femur with the pelvis, wherein the ball-shaped head of the femur is positioned within a socket-shaped acetabulum of the pelvis. The head of the femur or ball fits into the acetabulum, forming a joint which allows the leg to move forward, backward and sideways in a wide range of motion. The acetabulum is lined with cartilage, which cushions the bones and allows the joint to rotate smoothly and with minimal friction. An envelope of ligaments connect the pelvis and femur, covering the joint and stabilizing it. The cartilage also renders the joint sufficiently strong to support the weight of the upper body, and sufficiently resilient to absorb the impact of exercise and activity. A healthy hip allows the leg to move freely within its range of motion, while supporting the upper body and absorbing the impact that accompanies certain activities. Various degenerative diseases and injuries may require replacement of all or a portion of a hip using synthetic materials. Prosthetic components are generally made from any or combinations of metal, ceramic, and/or plastic material.

Total hip arthroplasty and hemi-arthroplasty are two procedures well known within the medical industry for replacing all or part of a patient's hip. A total hip arthroplasty replaces both the femoral component and the acetabular surface of the joint, so that both a femoral prosthesis and an acetabular prosthesis are required. To replicate the natural kinematics of a hip joint, a total hip prosthesis has three parts: the stem, which fits into the femur and provides stability; the ball, which replaces the spherical head of the femur; and an acetabular prosthesis, which replaces the hip socket. Each part is available in various sizes in order to accommodate a range of body sizes and types. In some designs, the stem and ball are one piece; other designs are modular, allowing for additional customization in fit.

A conventional acetabular prosthesis may include a cup, a cup and a liner, or in some cases only a liner, all of which may be formed in various shapes and sizes. Generally, a metal cup and a polymeric liner are used. The liner may be made of a variety of materials, including polyethylene, ultra high molecular weight polyethylene, metal, and ceramic materials. The cup is usually of generally hemispherical or partially hemispherical in shape and features an outer surface and an inner surface that is adapted to receive a cup liner. The liner fits inside the cup and has inner and outer surfaces. The cup liner is the bearing element in this type of acetabular component assembly. The outer surface of the liner corresponds to the inner surface of the cup or acetabulum, and the liner inner surface receives the head of a femoral component. An acetabular cup may include a highly polished inner surface in order to decrease wear.

The liner inner surface can be characterized by features relative to an axis, such as an axis of rotation through the center of the inner surface. This axis may or may not be aligned with the central axis or axis of rotation of the cup. In a typical liner the inner surface has a hemispherical or partially hemispherical geometry and is also referred to as the internal diameter. In such liners, the geometry of the internal diameter can be characterized as concentric to an axis that runs through the center of the internal diameter such as the axis of rotation of the cup, outer diameter of the liner or otherwise.

An acetabular prosthesis may be fixed in the reamed acetabulum of a patient. Such a prosthesis may include a cup (or a cup and liner assembly) that is fixed by placing screws or other retaining devices through apertures in the cup, by securing the cup with cement, or by using bone ingrowth material on the outer surface of the cup. In other cases, spikes, pegs, or fins around the rim of the cup are used to help hold the implant in place until new bone forms. In some cases, only a liner is cemented in a patient due to poor bone stock. Any combination of these structures or techniques may be used.

A femoral prosthesis used in total hip arthroplasty generally includes a spherical or near-spherical head attached to an elongate stem with a neck connecting the head and stem. In use, the elongate stem is located in the intramedullary canal of the femur and the spherical or near-spherical head moves in a manner corresponding to relative motion between the pelvis and femur, ("articulates") relative to the acetabular component. Femoral prostheses used in total hip arthroplasty procedures may or may not differ from a prosthesis used in a hemi-arthroplasty, described below. However, the femoral head of each type prosthesis is generally a standard size and shape. Various cups, liners, shells, stems and other components may be provided in each type arthroplasty to form modular prostheses to restore function of the hip joint.

Hemi-arthroplasty refers to replacing part of a hip joint, such as replacing a femoral component so that a femoral prosthesis similar to those used in a total hip replacement articulates against natural body tissue in the patient's acetabulum. In most cases, the acetabulum is left intact and the head of the femur is replaced, using a component similar to those employed in a total hip replacement. In other cases, a hemi-surface prosthesis fits over the head of the femur so that the bone of the femoral head is spared. This hemi-surface prosthesis is then fixed to the femur with cement around the femoral head and has a short stem that passes into the femoral neck. Generally, a femoral prosthesis implanted during a hemi-arthroplasty is referred to as an endoprosthesis and includes a stem and a head, and may include additional components such as shells and liners. Current designs include monoblock, and two, three and five component designs. A monoblock endoprosthesis is a one-piece structure including a femoral stem and head. Polarity refers to the number of articulating surfaces a prosthesis contains.

A monoblock endoprosthesis has one articulation surface between the head and the patient's natural acetabulum, and is therefore referred to as monopolar. Thus, a prosthesis may be described both with respect to the number of components and with respect to the number of articulating surfaces as installed in a patient. Some current designs may also include a mechanical device, such as a snap-ring, for constraining the femoral head, further described below.

Prostheses used in hip replacement surgery may also be described as constrained and non-constrained prostheses. Non-constrained prostheses rely on the downward force of the body through the joint and the tension created by the soft tissue, including the muscles, ligaments and tendons, to retain the femoral head relative to the acetabular prosthesis in its implanted position. Non-constrained prostheses generally allow the greatest range of motion. Other prostheses include mechanisms for preventing dislocation of the stem head from the acetabular component. Typically, these prostheses have restraint mechanisms that result in a smaller range of motion of the hip joint, and are generally referred to as "constrained" components. Dislocation may be the result of trauma to the hip, abnormal anatomy, soft tissue laxity, or impingement.

One example of a restraint mechanism is a shell or liner having greater than hemispherical coverage around the head such that the head is constrained within the internal diameter, thus preventing subluxation and dislocation. In contrast to standard liners, constrained liners may employ an extended, elevated portion over a segment of the periphery of the liner internal diameter in order to increase coverage of the femoral head and thus reduce the likelihood of dislocation and aid in reduction of the head should subluxation occur. While use of a constrained components is generally not desirable due to resulting decreased range of motion, the use of constrained components may be beneficial in cases of tenuous stability in order to avoid dislocation. See e.g. T. Cobb, et al., *The Elevated-Rim Acetabular Liner in Total Hip Arthroplasty: Relationship to Postoperative Dislocation*, Journal of Bone and Joint Surgery, Vol. 78-A, No. 1, January, 1996, pp. 80–86, which is incorporated by reference herein. However, constrained components reduce the range of motion in part because of the elevated lip segment; there is thus a substantial loss of overall range of motion compared to a standard liner. An implant stem head constrained by a shell or liner may dislocate if the femoral component rotates beyond the range of motion permitted by the assembly. Dislocation may occur because the edge or lip of the liner or shell that retains the implant stem head acts as a fulcrum about which the femoral component pivots, thereby causing the implant stem head to dislocate from its position within the liner or shell of the prosthesis. Dislocation of a hip prosthesis is painful and often requires medical intervention. Finally, a liner utilized in a constrained component must have a strong lock mechanism for retention in the cup due to the forces exerted on the liner by the other components of a constrained prosthesis. Lever out force is the moment required to dislocate the head from the liner. The ability of a prosthesis, such as an implant stem head, to withstand forces exerted on the liner is referred to as lever-out, or shuck-out. Pull out force is generally a tensile force applied in the direction of the rotational axis of the cup so as to separate the head from the cup.

During a total hip replacement procedure, the surgeon generally obtains measurements to ensure proper prosthesis selection, limb length and hip rotation. After making the incision, the surgeon works between the hip muscles to gain access to the joint. The femur is pushed out of the acetabulum and removed so that the exposed joint cavity may be cleaned and enlarged with reamers of gradually increasing size. The cup of the acetabular prosthesis is then placed in the prepared hemispherical socket. A liner may then be inserted into the cup and fixed into place. The femur is then prepared to receive the stem by reaming the center of the bone and planing and smoothing the top end of the femur. If the ball is a separate piece, the proper size is selected and attached. The assembled femoral component is then placed within the acetabular component and the joint is properly aligned. If complications such as dislocation require a surgeon to perform a revision procedure and utilize a constrained component, the surgeon may be forced to remove the acetabular component in its entirety, causing damage and bone loss.

Current constrained liner designs have many disadvantages. One design currently used does not adequately constrict movement of the components, resulting in component wear. Also, some current constrained liners are not easily removable after installation in a patient because the mechanism retaining the components is not easily accessible or reverse-operable. Other locking mechanisms are located on the exterior surface of the assembly, allowing deformation and dislocation of the locking mechanism and subsequent failure of the component. Finally, currently available designs do not offer both adequate range of motion and sufficient lever-out.

Thus, there is a need for a constrained liner assembly that offers both adequate range of motion and sufficient lever-out.

There is also a need for a constrained liner assembly that is easily disassembled after installation in a patient.

There is also a need for a constrained liner assembly that allows an existing, implanted acetabular shell to be converted to a constrained prosthesis without requiring removal of the shell and thus damage to the patient's bone and other structures.

Finally, there is a need for a liner assembly that is capable of reducing the movement of components, in order to decrease wear of the components.

These are some needs which exist in conventional designs, one, some or all of which needs are fulfilled by some or all structures of various embodiments of the invention.

SUMMARY

Methods, systems and devices according to this invention seek to prevent prosthetic components from separating from each other. They also seek to provide improved orthopedic prosthetic components and more specifically, improved constrained components that may be utilized with existing implanted prosthetic components. Liner assemblies and systems according to various embodiments of this invention include an adapter component designed to link current prosthetic cup geometry to a constrained liner, so that implanted prosthetic cups may be retrofit with a constrained liner, while providing optimal range of motion and sufficient lever out. Liner assemblies and systems according to various embodiments of this invention provide a sufficient range of motion without sacrificing lever out.

Certain embodiments of an adapter component according to this invention include first and second adapter elements and a locking member. The first adapter element is adapted to engage a prosthetic cup, and is adapted to receive the locking member. The first and second adapter elements include opposing tapers, so that when assembled, a taper lock is formed by the two elements. As assembled, the locking member of the adapter component couples the adapter component and the liner, retaining the liner in position.

Certain embodiments of this invention also include a constrained liner assembly having structure designed to couple an implant stem head to a cup. Components of a liner assembly according to this invention may include an adapter component, a liner, including a retaining member, and a capture member. An adapter component is coupled to a prosthetic cup, and a liner is inserted into the adapter component and cup. An implant stem head is inserted into the liner, deforming a retaining member housed in a channel in the liner. A capture member is inserted into slots on the liner, deforming the retaining member and retaining the implant stem head in position in the liner.

DETAILED DESCRIPTION

Various methods, systems and devices according to this invention seek to provide improved orthopedic prosthetic components and more specifically, improved constrained components that may be utilized with existing implanted prosthetic components. Liner assemblies and systems according to certain embodiments of this invention may include an adapter component designed to link current prosthetic cup geometry to a constrained liner, while providing optimal range of motion and sufficient lever out. Generally, a liner assembly according to certain embodiments of this invention includes an adapter component designed to resist disassembly as force is applied to the assembly.

Liner assemblies according to certain embodiments of this invention includes structure designed to couple an implant stem head to a cup. The components of the liner assembly generally include an adapter component, a liner, including a retaining member, and a capture member. For example, in one embodiment, an adapter component includes first and second adapter elements having opposing tapers, so that when assembled, a taper lock is formed by the two elements. In one embodiment, the first adapter element and the cup include opposing tapers, so that when the adapter element is assembled and inserted into the cup, a taper lock is also formed between the adapter component and the cup. In one embodiment, the first adapter element includes geometry permitting the first adapter element to mate with the cup. In one embodiment, a locking member of the adapter component couples the first adapter element and the liner, retaining the liner in position.

Figure 1:
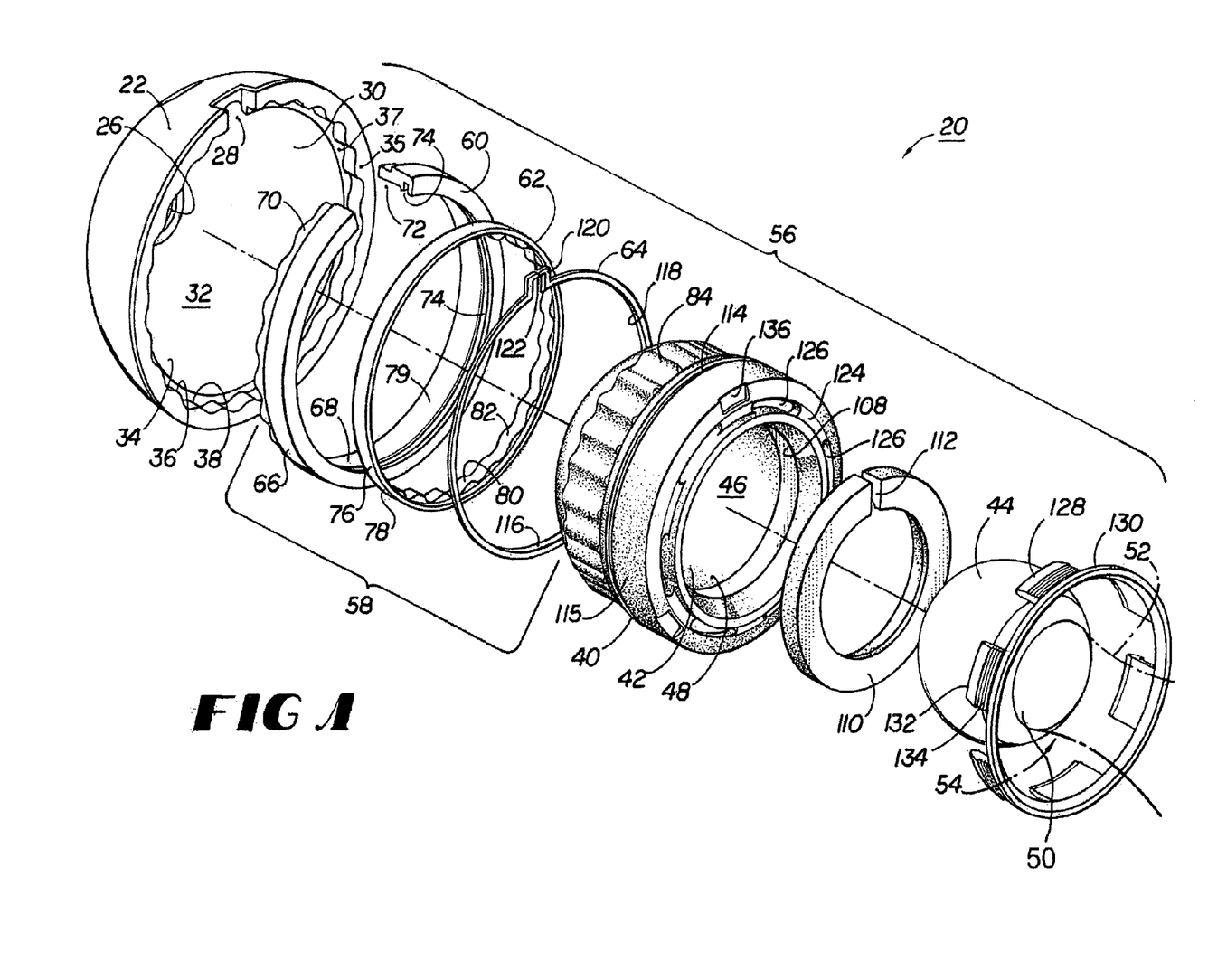
FIG. 1 is an exploded perspective view of a prosthesis according to one embodiment of this invention.
Figure 2:
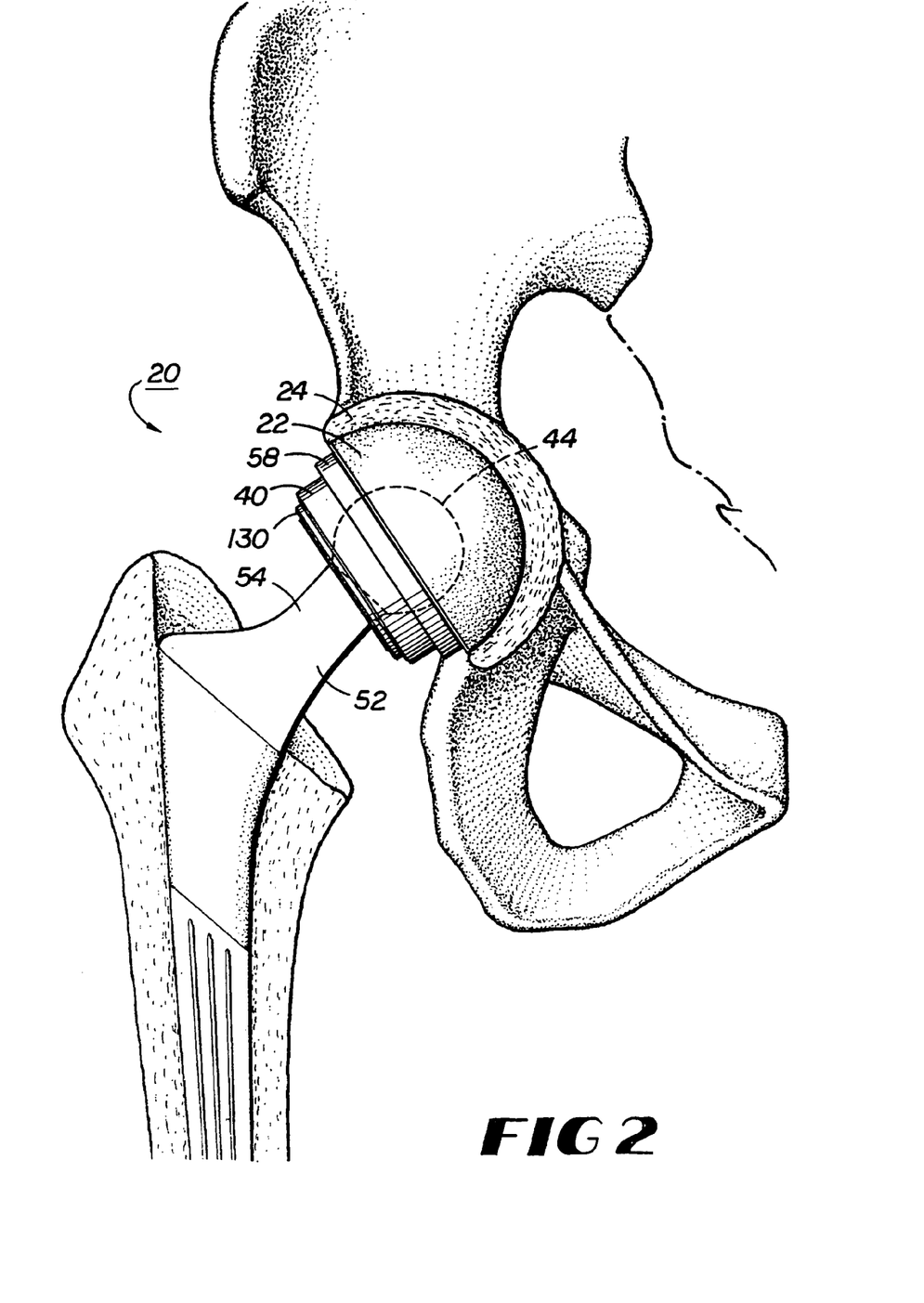
FIG. 2 is a partially sectional front elevation view of the prosthesis of FIG. 1, assembled and implanted.
Figure 3:
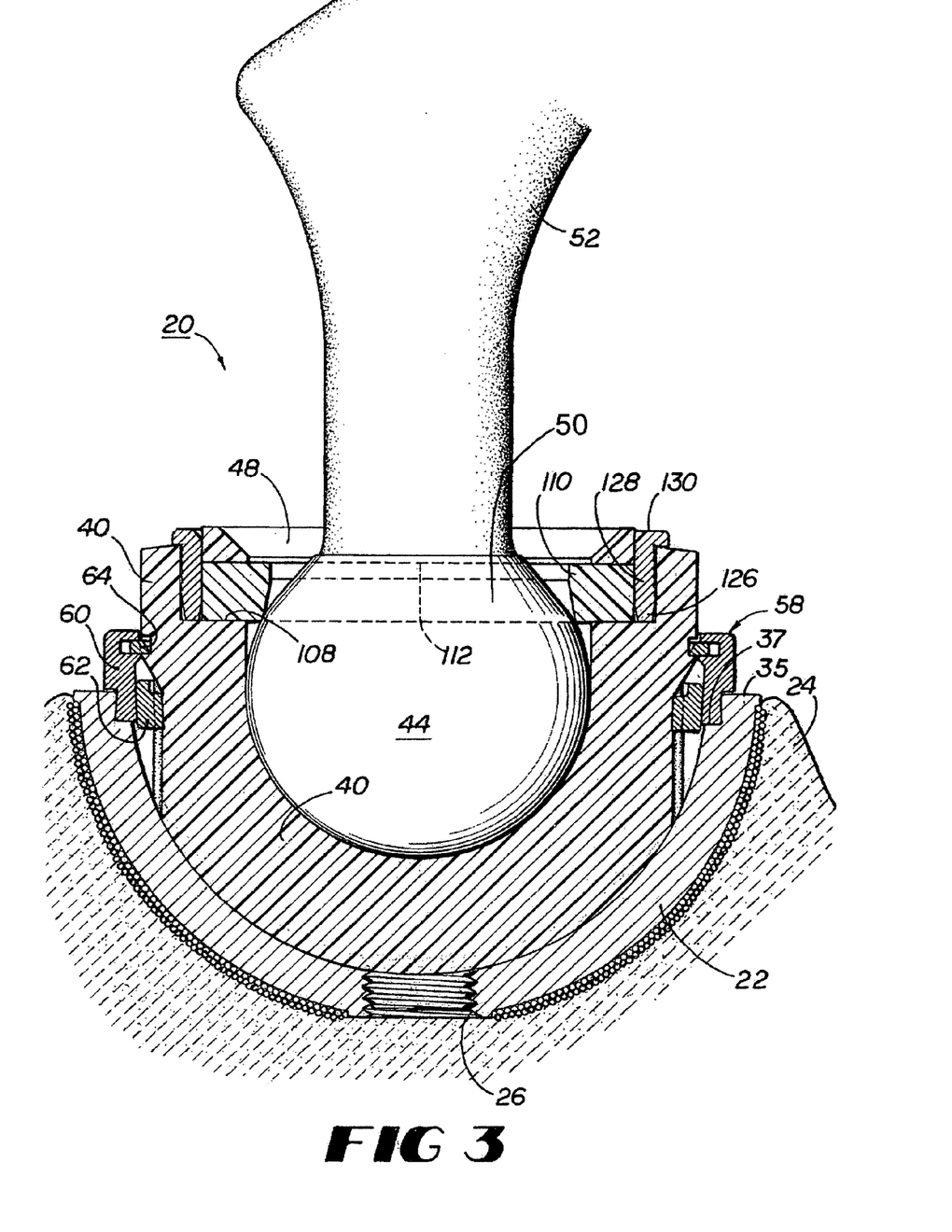
FIG. 3 is a cross-sectional view of the prosthesis of FIG. 1.

Consider one example of systems and devices according to this invention. As shown in FIGS. 1–3, hip prosthesis 20 includes a first implant structural member, such as an acetabular cup 22, which is adapted to fit within acetabulum 24 and adapted to capture and retain a second implant structural member, such as a liner. Cup 22 includes an apex hole 26, a removal slot 28 and a cavity 30 that has a generally spherical shape and that is formed by an inner surface 32 and an opening 34. Cup 22 also includes a first surface 35 on the face of the cup and a second surface 37. The inner surface 32 of the cup 22 includes geometry that is adapted to mate with geometry of a liner or of an adapter component, further described below. In one embodiment, the inner surface 32 of the cup 22 includes splines 36 and taper 38, adapted to mate with an adapter component, further described below. The cup cavity 30 is adapted to receive a liner 40, which includes a liner cavity 42 adapted to receive implant stem head 44. The cavity 42 of the liner 40 is defined by an inner surface 46 and an opening 48. The inner surface 46 of the liner 40 may be formed from any conventional process.

The implant stem head 44 is generally spherical in shape and includes cavity 50, which is adapted to receive a femoral stem 52, the implant stem head 44 and femoral stem 52 forming a femoral prosthetic component 54 when assembled. The cavity 50 of the implant stem head 44 may be generally cylindrical, conical, cubical, or any other suitable shape. In other alternative embodiments, the cavity 50 may include threads, barbs, rings or any other suitable mechanical connectors to couple the head 44 to the stem 52. In yet another embodiment, adhesive or cement may be used to couple the head 44 to the femoral stem 52. The components of the various prostheses described may be made from metal, such as stainless steel and titanium, ceramic, plastic, such as polyethylene, or any other suitable material. In one embodiment, the cup and implant stem head are either metal or ceramic, while the liner is polyethylene. In other embodiments, the liner is metal or ceramic. In yet another embodiment, the liner is plastic and includes a metal outer surface.

Figure 4:
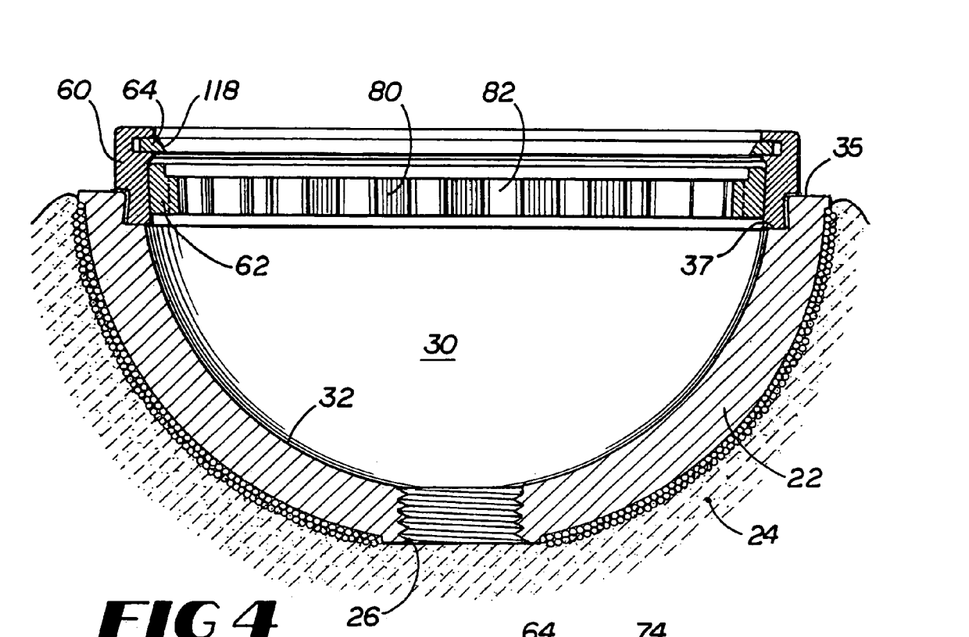
FIG. 4 is a cross-sectional view of the adapter component and cup of FIG. 1.
Figure 5:
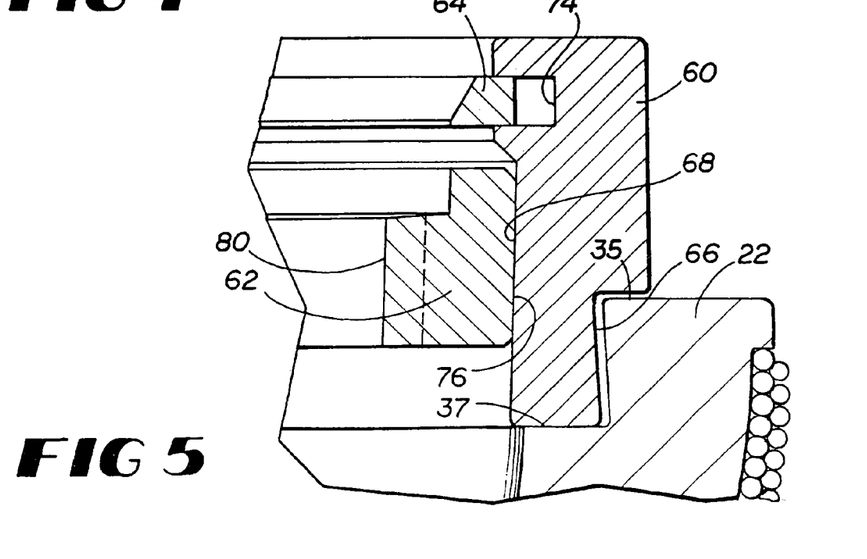
FIG. 5 is an enlarged fragmentary cross-sectional view of the components of FIG. 4.

A liner assembly 56, shown in FIGS. 1–3, includes an adapter component 58 having a first adapter element 60, a second adapter element 62, and a locking member 64, all of which may be made from metal, or any other suitable material. As shown in FIGS. 4 and 5, first adapter element 60 includes an outer surface 66 and an inner surface 68. In one embodiment, both the outer and inner surfaces are tapered. In one embodiment, each taper is a 5 degree taper. In another embodiment, any suitable taper may be used. In another embodiment, the outer surface 66 is not tapered. In one embodiment, the outer surface 66 of the first adapter element 60 includes geometry adapted to mate to geometry on cup 22. In one embodiment, the outer surface 68 of the first adapter element includes splines 70 to match the splines 36 on the inner surface 32 of acetabular cup 22, as shown in FIGS. 1–3. In this embodiment, the splines allow rotation of the assembly in order to change geometry. In addition to the contact of outer surface 66 to cup 22, in the embodiment shown in FIG. 3, first adapter element 60 contacts second surface 37 of cup 22. In alternative embodiments, outer surface 66 contacts cup 22 and first adapter element 60 also contacts cup 22 at both surfaces 35, 37 or only at surface 35. First adapter element 60 also includes opening 72, allowing the first adapter element to deform, and a recess 74 adapted to receive and house a locking member 64, further described below.

As shown in FIGS. 4 and 5, the outer surface 76 of second adapter element 62 includes a taper 78 that mates with the inner surface taper 79 of first adapter element 60. In one embodiment, each taper is a 5 degree taper. In another embodiment, any suitable taper may be used. As the second adapter element 62 is urged toward and engages the first adapter element 60, the opening 72 of the first adapter element 60 is expanded, so that the splines 70 and taper 79 on the outer surface 66 of the first adapter element 60 are locked into the splines 36 and taper 38 on the inner surface 32 of the cup 22. In this manner, first and second adapter elements mate and wedge into the splines 36 on the inner surface 32 of the cup 22, and the adapter component 58 is engaged in cup 22.

In one embodiment, the inner surface 80 of the second adapter element 62 includes geometry that mates with geometry on the liner 40, providing alignment and rotation resistance of the liner. In one embodiment, the inner surface 80 of the second adapter element 62 includes splines 82 that mate with splines 84 on the outer surface of the liner 40, as shown in FIG. 3. In an alternative embodiment, the inner surface of the second adapter element does not engage the liner. In this embodiment, the liner may mate only with the locking member or with the cup or first adapter element. For example, a cup may include fins on the inner surface of the cup to lock the liner in position. In one embodiment, outer surface 76 of second adapter element 62 includes any suitable taper.

Figure 6:
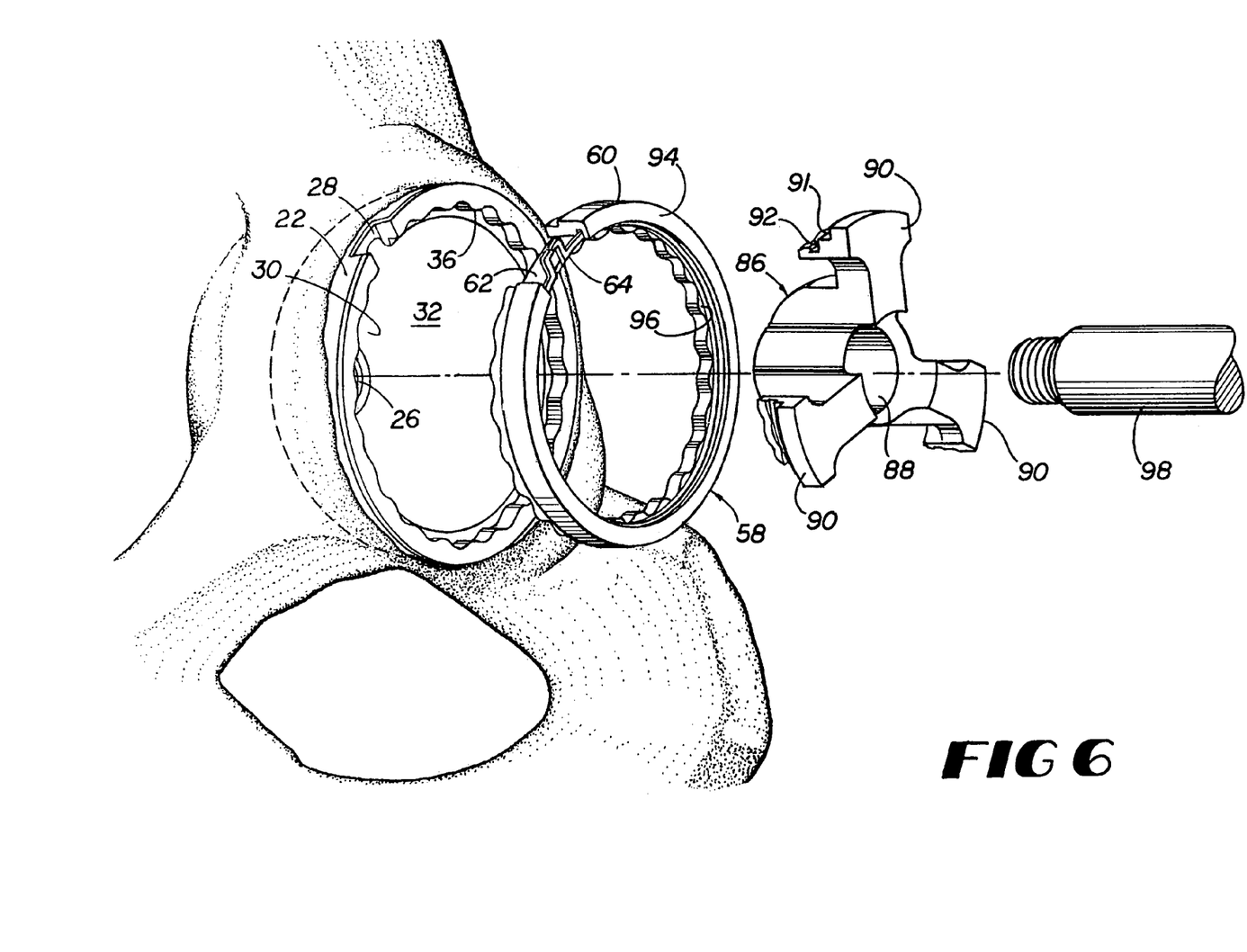
FIG. 6 is an exploded perspective view of an adapter component and cup, together with a positioning element and alignment rod according to one embodiment of this invention.

In one embodiment, a positioning element 86 is used to position and align the first and second elements 60, 62 of the adapter component 58 in order to accurately position the elements for engagement and locking. In one embodiment, the positioning element 86 is a plastic member, shown in FIG. 6, having an aperture 88 and three arms 90, each for engaging the adapter component 58 as assembled. Each arm 90 includes first and second surfaces 91, 92. First surface 91 rests on a top surface 94 of the first adapter element, while second surface 92 rests on surface 96 of the second adapter element 62, so that each adapter element is properly aligned relative to the other adapter element. The three arms 90 are equally spaced, so that an equal amount of force is exerted and proper alignment and locking is obtained.

Figure 7:
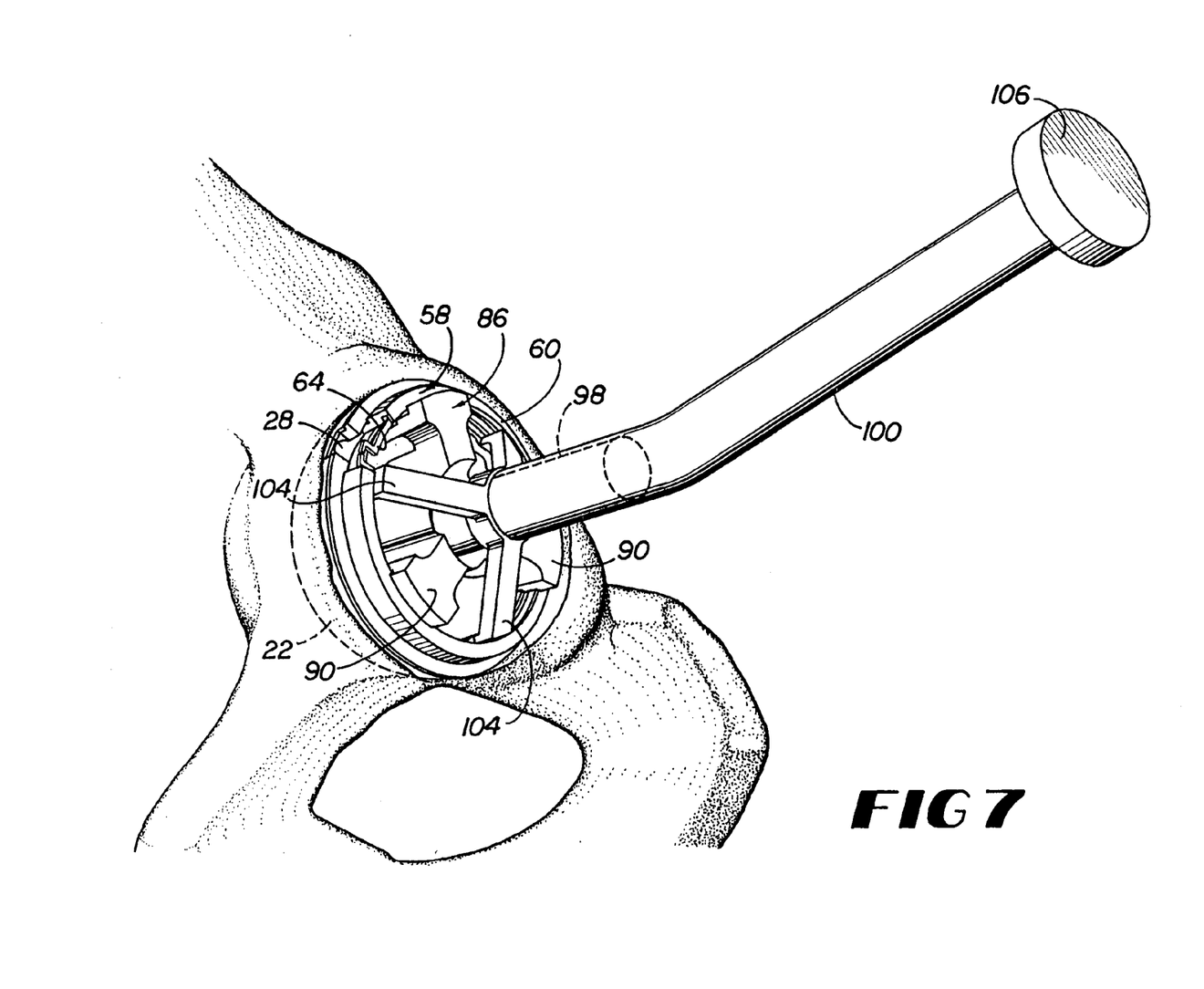
FIG. 7 is a perspective view of the components of FIG. 6, together with an impactor according to one embodiment of this invention.
Figure 8:
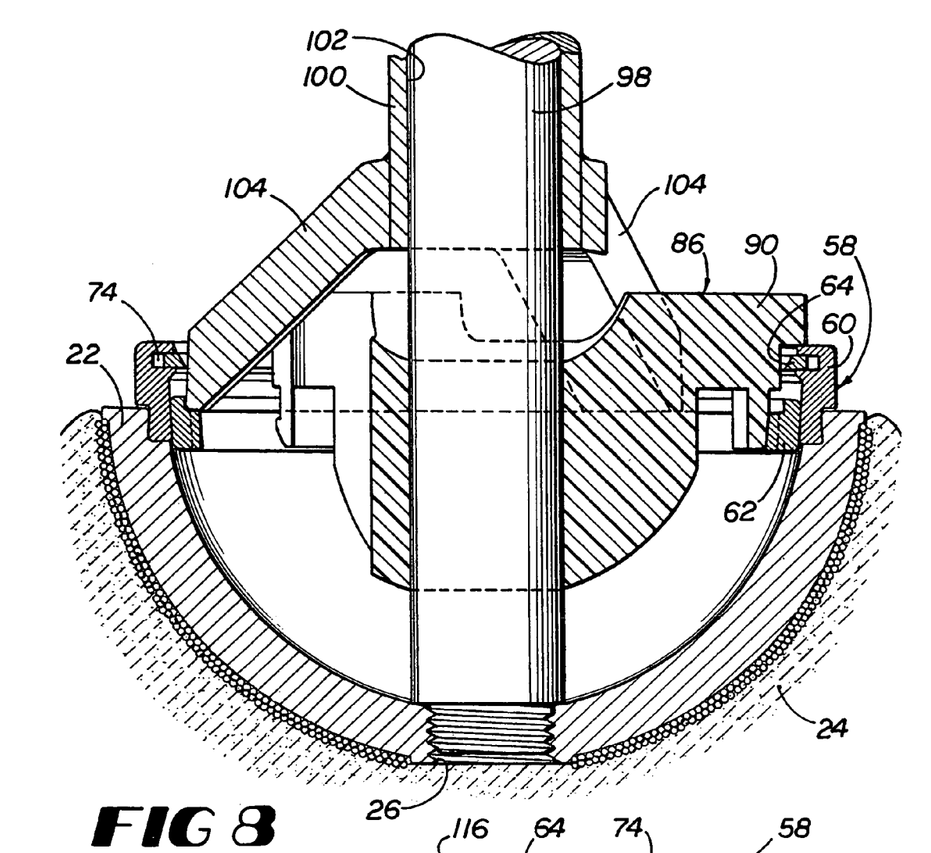
FIG. 8 is a cross-sectional view of the components and instruments of FIG. 7.
Figure 9:
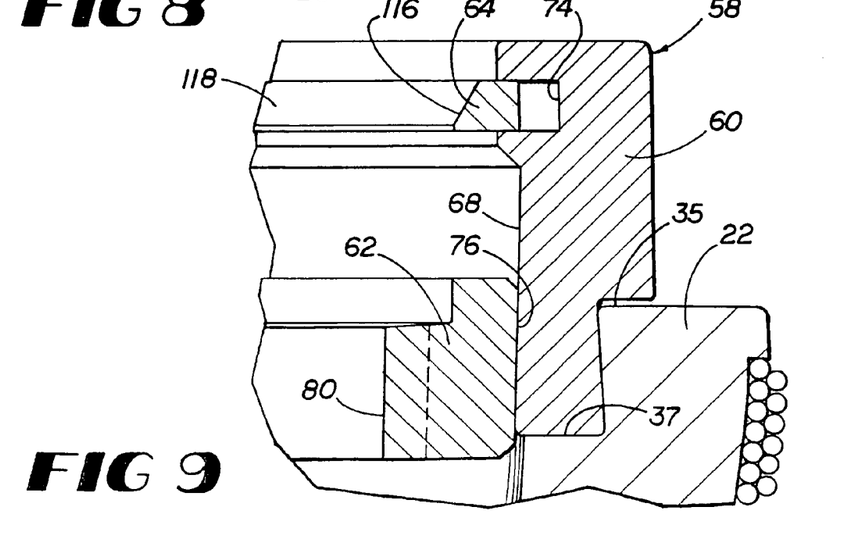
FIG. 9 is an enlarged fragmentary cross-sectional view of the components of FIG. 8.
Figure 10:
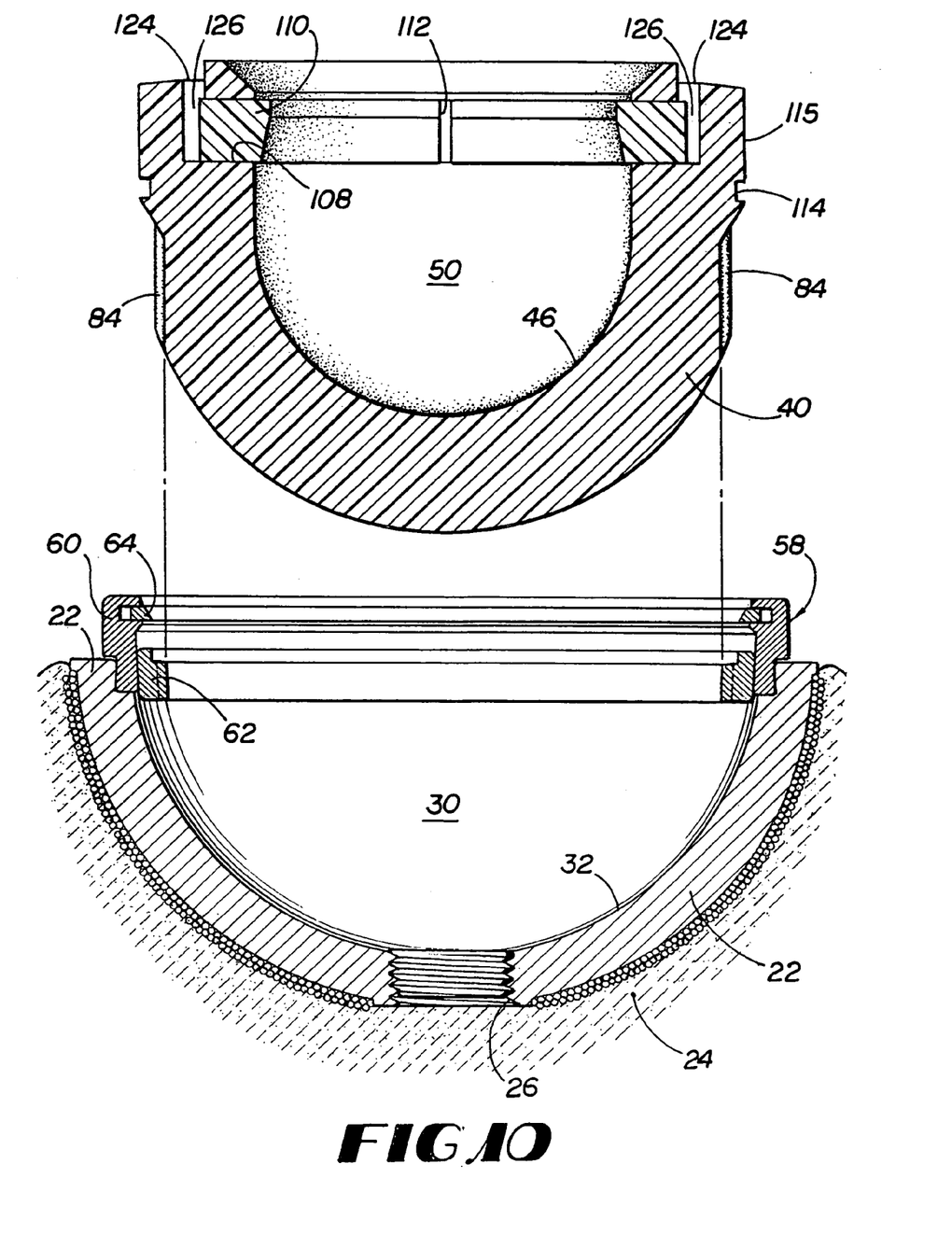
FIG. 10 is an exploded cross-sectional view of a liner and retaining member prior to insertion into an adapter component and cup.
Figure 11:
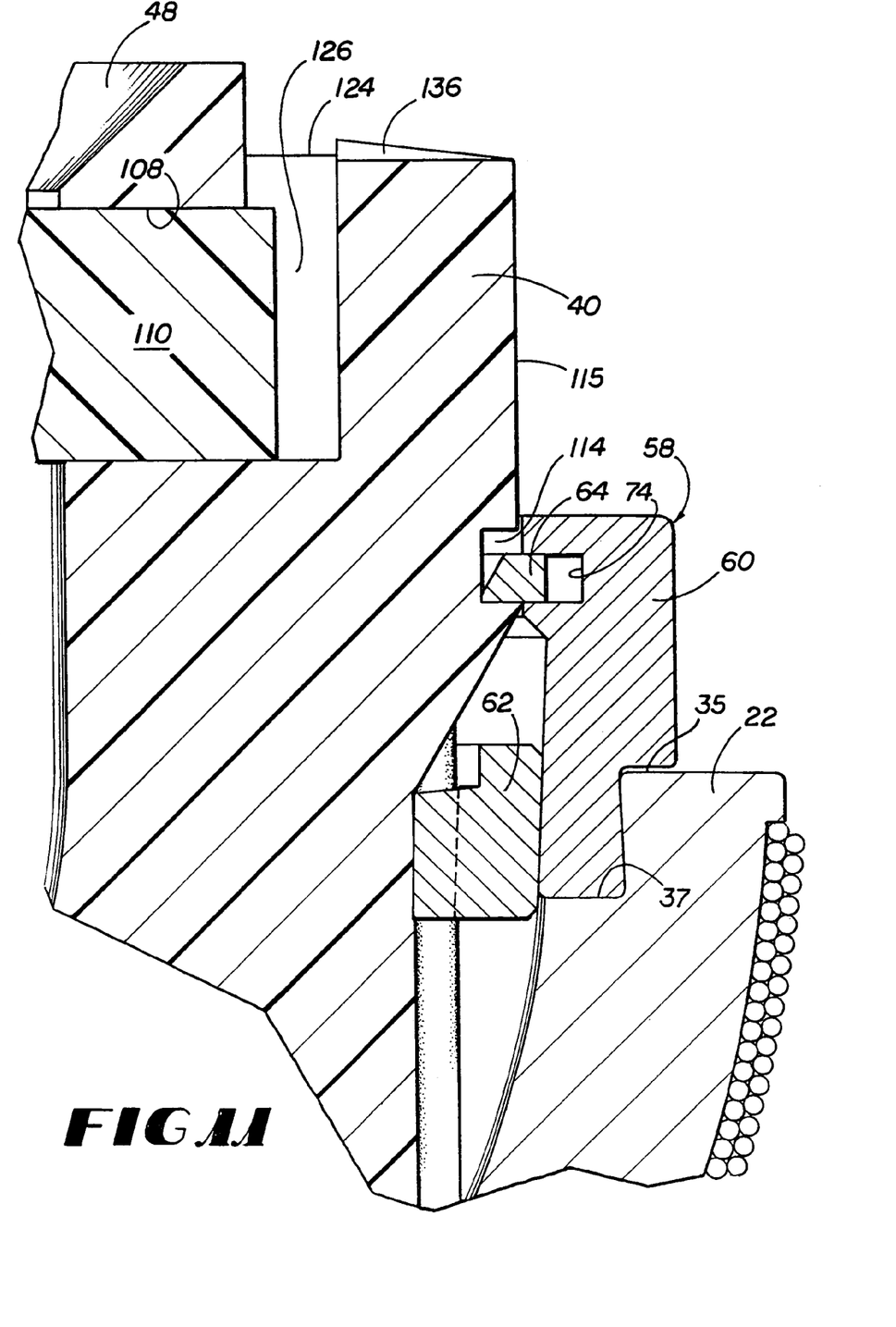
FIG. 11 is an enlarged fragmentary cross-sectional view of the components of FIG. 10.

In one embodiment, shown in FIGS. 6–9, the aperture 88 is centered and is adapted to receive an alignment rod 98, which is threaded to the apex hole 26 of the acetabular cup. As shown in FIGS. 7–9, an adapter component impactor 100 includes a bore 102 that is adapted to receive the alignment rod 98. The legs 104 of the impactor 100 may be positioned between the arms 90 of the positioning element 86, and a mallet or other suitable instrument may be used to strike the platform 106 on the impactor 100. This force causes the second adapter element 62 to move toward the first adapter element 60 so that the two elements are locked. As described above, this coupling of the two adapter elements 60, 62 expands the first adapter element 60 into locking position in cup 22, as shown in FIGS. 8–9. In another embodiment, an alignment device is included on the impactor, and a separate positioning element is not used.

As shown in FIGS. 1–3 and 10, liner 40 includes a liner cavity 42 adapted to receive an implant stem head 44. Liner 40 also includes channel 108 adapted to house a retaining member 110. In one embodiment, retaining member 110 is made of a deformable material, such as polyethylene or any other suitable material, so that slit 112 of retaining member 110 allows retaining member 110 to deform adequately to be inserted into channel 108 of liner 40. Slit 112 of retaining member 110 also allows the retaining member 110 to expand to permit insertion of implant stem head 44. Slit 112 then contracts as the implant stem head 44 passes through retaining member 110 into the cavity 42 of the liner 40. In one embodiment, the liner 40 is provided with the retaining member 110 located in the channel 108. Liner 40 may be made from plastic, ceramic, or metal, or any other suitable material.

As shown in FIGS. 10–13, liner 40 (including retaining member 110 in channel 108) is inserted into the assembled adapter component 58 and cup 22. As shown in the Figures and as discussed above, the adapter component 58 includes a locking member 64 housed in a recess 74 of the first adapter element 60. The locking member 64 is also received in a groove 114 on the outer surface 115 of the liner 40, and, in one embodiment, includes a taper 116 on the inner surface 118 of the locking member 64. The locking member 64 includes a projection 120 having a opening 122, which allows the locking member 64 to expand to receive the liner 40. When the liner 40 is inserted into the adapter component 58 and the cup 22, the locking member 64 is compressed in the groove 114 of the liner 40, so that the liner 40 is retained in the adapter component 58.

Figure 12:
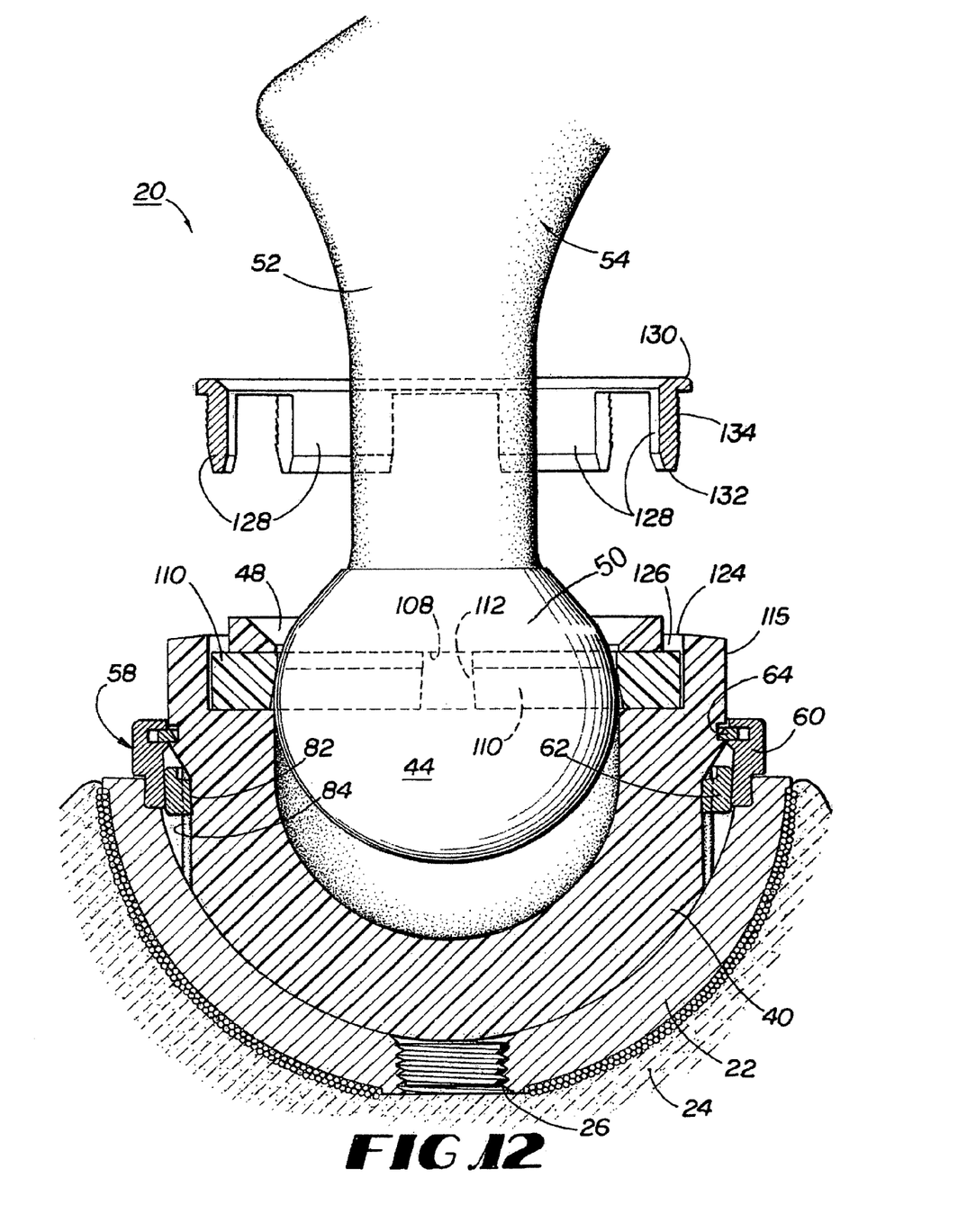
FIG. 12 is a partially exploded cross-sectional view of the stem head being inserted into the liner of FIG. 1.
Figure 13:
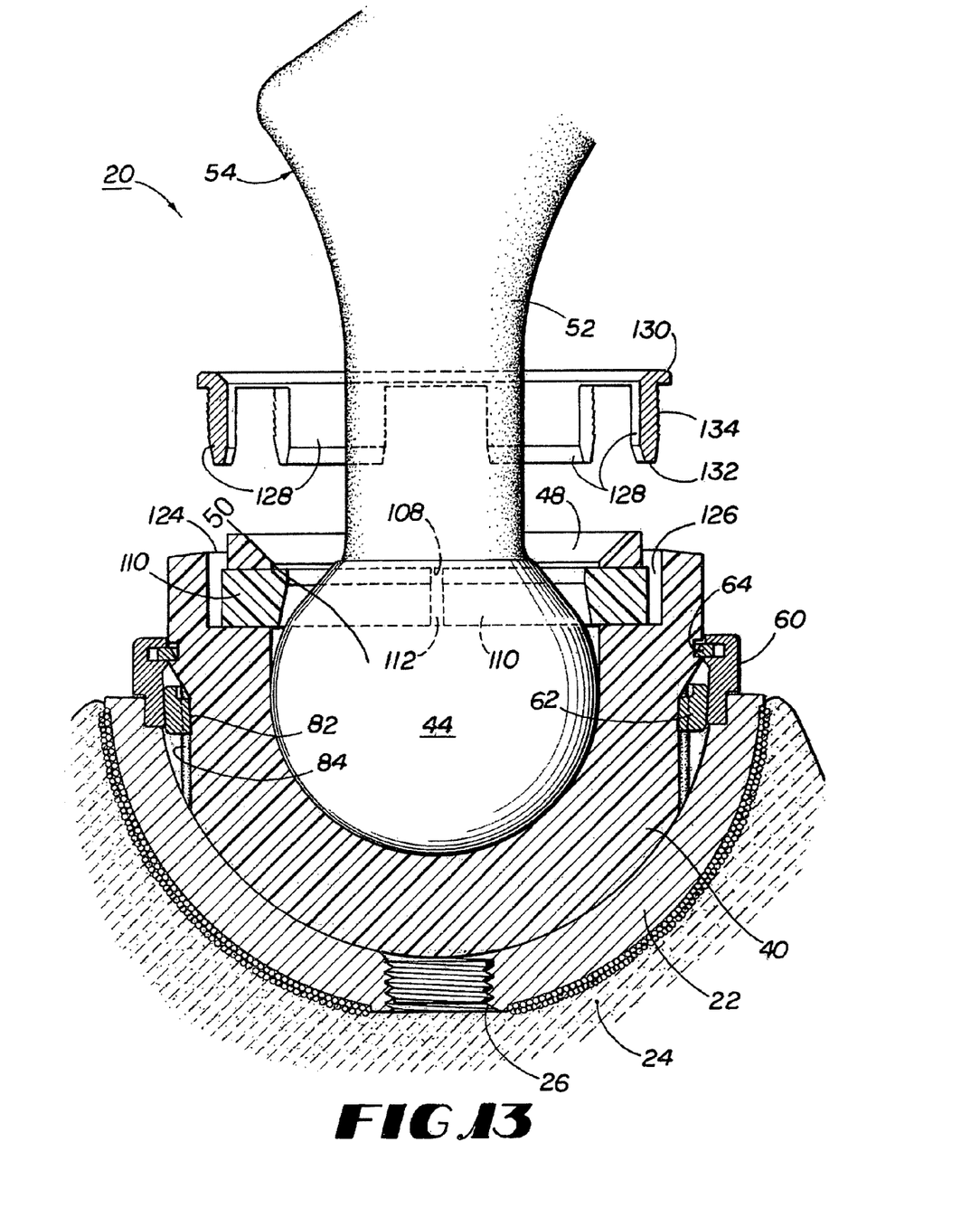
FIG. 13 is a cross-sectional view of the prosthesis of FIG. 12, after insertion of an implant stem head, with the capture member disposed above the liner.

The face 124 of the liner 40 includes slots 126 adapted to receive the tabs 128 of a capture member 130, as shown in FIGS. 12–13. In one embodiment, the capture member 130 is metal. In another embodiment, the capture member 130 is made from any other suitable material. Each tab 128 includes tapered end 132 and serrated surface 134, which assist in retaining the tabs 128 in position in slots 126. The liner 40 includes a capture member removal notch 136 so that the capture member 130 may be removed easily, even after implantation of the prosthetic components. The tabs 128 of capture member 130 are inserted into slots 126 of liner 40 after implant stem head 44 is inserted into the cavity 42 of liner 40. An impactor is used to press fit capture member 130 into engagement with liner 40. In this manner, the capture member 130 compresses the retaining member 110, preventing slit 112 in retaining member 110 from expanding, and thereby retaining implant stem head 44 in cavity 42 of liner 40.

In an alternative embodiment, a metal or ceramic liner is coupled to an implant stem head and an acetabular cup. In this embodiment, a single adapter element is coupled to a cup, and a liner is press fit into a taper lock engagement with the cup and adapter element.

In another alternative embodiment, the adapter component includes a first adapter element and a locking member. In this embodiment, a second adapter element is included in the liner, so that insertion of the liner locks the adapter elements and retains the liner in the cup.

In another alternative embodiment, the liner does not include a retaining member. In this embodiment, the cavity of the liner is of sufficient diameter to receive an implant stem head without deformation of the liner. A capture member is inserted into slots on the face of the liner, deforming the plastic liner toward the implant stem head and thereby retaining the head in the liner.

A liner assembly according to embodiments of this invention is removable in steps, without destroying the individual components of the assembly and without requiring removal of the femoral or acetabular implants. Components of the liner assembly may be removed using a standard removal tool, or any other suitable tool. In addition, a liner assembly according to one embodiment of this invention may be used to retrofit an implanted acetabular cup as a constrained device.

One method of using one form of structure according to this invention is as follows:

For a surgical revision of an implanted hip prosthesis, the existing prosthetic liner is removed using a liner removal tool and the apex hole cover of the acetabular cup is removed using a device such as a screwdriver. The method described may also be used for a primary hip arthroplasty, wherein the acetabulum is prepared and a cup is inserted, using any screws, pegs or other devices, according to the prescribed surgical technique.

As shown in the Figures, an appropriately sized adapter component 58, including first and second adapter elements 60, 62 and a locking member 64, is chosen. After placing the locking member 64 in recess 74 of first adapter element 60 and locating second adapter element 62 adjacent first adapter element 60, a positioning element 86 is placed on adapter component 58 to ensure proper alignment of the cup 22 and the adapter component 58, and of the first and second adapter elements 60, 62. Before mating with the second adapter element 62 and insertion into cup 22, first adapter element 60 is in a first position, as shown in FIG. 4, so that opening 72 is compressed, providing an outside diameter that allows insertion of the adapter component 58 into cup 22.

The adapter component 58 is inserted into the cup 22 so that the adapter component 58 mates with the existing cup geometry, in this embodiment, splines 36, until an audible click is heard. In general, for ease of insertion, the open end of the adapter component is inserted over the removal slot 28 of the cup 22, or where best visibility of opening is possible. An alignment rod 98 is inserted and is threaded to the apex hole of the cup 22 either by hand or with a screwdriver. A hollow impactor slides over the alignment rod 98 and the legs 104 of the impactor 100 are positioned between the arms 90 of the positioning element 86. A mallet is used to strike the platform 106 on the impactor 100 until sufficient force causes the second adapter element 62 to be driven off of the positioning element 86 and to be urged toward and locked into the first adapter element 60. This engagement of the first and second adapter elements 60, 62 expands the outer diameter of the first adapter element 60 so that the first adapter element 60 engages the cup 22, as shown in FIG. 9. After installation of the adapter component 58, the positioning element 86 may be removed and discarded, and hole covers may be inserted into the cup, if required.

The assembled liner 40 and retaining member 110 are then inserted into the assembled cup 22 and adapter component 58. Rotation of the liner may be required to obtain optimal positioning. A liner impactor tool is used to completely seat the liner 40, forcing the locking member 64 into the groove 114 on the liner 40, holding the liner 40 in position in the cup 22.

An appropriately sized implant stem head 44 and femoral stem 52 are chosen and assembled as femoral component 54. The capture member 130 is then placed over the implant stem head 44 of the femoral component 54 so that the tabs 128 face away from the femur. The implant stem head 44 of the femoral component 54 is placed into the cavity 42 of the liner 40 and rotated to check mobility of the implant stem head 44 in the liner 40. Retaining member 110 expands to allow insertion of implant stem head 44 and contracts after implant stem head 44 passes into cavity 42 of liner 40. The tabs 128 of capture member 130 are then positioned on the slots 126 on the face 124 of the liner 40 and pressed into the slots 126 of the liner 40, using an impactor to fully seat the capture member. After insertion, the capture member 130 compresses retaining member 110, capturing and retaining implant stem head 44 in cavity 42.

A hip prosthesis incorporating a liner assembly according to embodiments of this invention offers advantages over current designs, including increases in lever out values and allowed range of motion, in part based on the fact that designs according to embodiments of this invention allow larger stem head sizes to be used for a given cup, than do conventional designs. Liner assemblies according to embodiments of this invention provide a desirable compromise between lever out values and range of motion, affording a sufficient range of motion without sacrificing lever out. The chart below summarizes various parameters for various sources for a hip prosthesis according to one embodiment of this invention and for three separate designs that are currently available.

| | Liner Assembly | Product 1 (various mm head, 10° liner) | Product 2 (28 and/or 32 mm head) | Product 3 (32 mm head, 10° liner) |
| --- | --- | --- | --- | --- |
| Pull-out (Head from liner) | 237 lbs$^{22\ mm}$ 291 lbs$^{26\ mm}$ 257 lbs$^{28\ mm}$ 268 lbs$^{32\ mm}$ | 300 lbs 331 lbs | 300 lbs$^{(28\ mm)}$ 325 lbs$^{(28\ mm)}$ 600 lbs$^{(32\ mm)}$ 273 lbs$^{(avg)}$ | 361 lbs 351 lbs |
| Lever-Out (Head from liner) | 191 in-lbs$^{22\ mm}$ 249 in-lbs$^{26\ mm}$ 271 in-lbs$^{28\ mm}$ 215 in-lbs$^{32\ mm}$ | 270/410 in-lbs | 150 in-lbs$^{(28\ mm)}$ | 622 in-lbs 178 lbs |
| ROM | +4 heads 73° w/46–56 mm$^{22\ mm}$ 79° w/50–60 mm$^{26\ mm}$ 87° w/54–68 mm$^{28\ mm}$ 94° w/62–68 mm$^{32\ mm}$ | 72° w/ 50–54 mm:$^{22\ mm}$ 84° w/ 56 mm:$^{26\ mm}$ 84° w/ 58–74 mm:$^{28\ mm}$ | 88° w/ 28 mm 98° w/ 32 mm 90° w/ 32 mm AML flexion/ extension = 102°/32 mm | 88° w/ 32 mm |
| Cup Size Range | 46–70 mm | 50–74 mm | 48–68 mm | 50–80 mm |

Various embodiments of a liner assembly as described above all relate to prostheses used in hip arthroplasty. Similar embodiments of a liner assembly according to this invention may be incorporated into other orthopedic prostheses. Alternative embodiments of a liner assembly according to this invention may be utilized to capture and retain other prosthetic components. As various changes could be made in the above structures and methods without departing from the scope of the invention as defined in the claims, it is intended that all matter contained in the above description or shown in the accompanying drawings be interpreted as illustrative and not in a limiting sense.

The invention claimed is:

1. A constrained liner assembly for use with an orthopedic prosthetic device, comprising:
   (a) an adapter component comprising
      a first adapter element having a first surface adapted to mate with a prosthetic cup, a second surface adapted to mate with a second adapter element and a recess adapted to receive a locking member,
      a second adapter element having a first surface adapted to mate with the second surface of the first adapter element, and
      a locking member; and
   (b) a liner component comprising
      a liner having a groove adapted to receive the locking member, a channel adapted to receive a retaining member, and a cavity adapted to receive an implant stem head,
      a retaining member having a slit, and
      a capture member adapted to compress the retaining member to retain an implant stem head in the cavity in the liner,
   wherein the adapter component couples the liner component to a prosthetic cup.

2. The constrained liner assembly of claim 1, wherein the second adapter element further comprises a second surface adapted to mate with an outer surface of the liner.

3. The constrained liner assembly of claim 2, wherein the second surface of the second adapter element is tapered.

4. The constrained liner assembly of claim 2, wherein the second surface of the second adapter element includes splines.

5. The constrained liner assembly of claim 1, wherein the second surface of the first adapter element is tapered and the first surface of the second adapter element is tapered, forming a taper locking interface between the first and second adapter elements when the elements are coupled.

6. The constrained liner assembly of claim 1, wherein the first and second adapter elements are rings.

7. The constrained liner assembly of claim 1, wherein the locking member is a locking ring.

8. The constrained liner assembly of claim 1, wherein the adapter component is metal.

9. The constrained liner assembly of claim 1, wherein the liner component is plastic.

10. The constrained liner assembly of claim 1, wherein the capture member is metal.

11. A prosthetic device for use in replacing at least part of a hip joint comprising:
    (a) a prosthetic acetabular cup;
    (b) a constrained liner assembly, comprising:
       (i) an adapter component comprising
       a first adapter element having a first surface adapted to mate with a prosthetic cup, a second surface adapted to mate with a second adapter element and a recess adapted to receive a locking member
       a second adapter element having a first surface adapted to mate with the second surface of the first adapter element, and
       a locking member; and
       (ii) a liner component comprising
       a liner having a groove adapted to receive the locking member, a channel adapted to receive a retaining member, and a cavity adapted to receive an implant stem head,
       a retaining member having a slit, and
       a capture member adapted to compress the retaining member to retain an implant stem head in the cavity in the liner,
    (c) a femoral component, comprising
       (i) an implant stem head adapted to approximate the size and shape of the head of a femur; and
       (ii) an implant stem component adapted to be fitted to a resected femur;
    wherein the constrained liner assembly couples the acetabular cup to the femoral component and wherein the constrained liner assembly provides resistance to disassembly.

12. A prosthetic device according to claim 11, wherein the second adapter element further comprises a second surface adapted to mate with an outer surface of the liner.

13. The prosthetic device of claim 11, wherein the second surface of the second adapter element is tapered.

14. The prosthetic device of claim 11, wherein the second surface of the second adapter element includes splines.

15. The prosthetic device of claim 11, wherein the second surface of the first adapter element is tapered and the first surface of the second adapter element is tapered, forming a taper locking interface between the first and second adapter elements when the elements are coupled.

16. The prosthetic device of claim 11, wherein the first and second adapter elements are rings.

17. The prosthetic device of claim 11, wherein the locking member is a locking ring.

18. The prosthetic device of claim 11, wherein the adapter component is metal.

19. The prosthetic device of claim 11, wherein the liner component is plastic.

20. The prosthetic device of claim 11, wherein the capture member is metal.

21. A method of replacing at least part of a hip joint in a patient, comprising:
    (a) selecting and assembling an appropriately sized adapter component, the adapter component comprising
       a first adapter element having a first surface adapted to mate with a prosthetic cup, and a second surface adapted to mate with a second adapter element, and
       a second adapter element having a first surface adapted to mate with the second surface of the first adapter element;
       wherein the second surface of the first adapter element is tapered and the first surface of the second adapter element is tapered, forming a taper locking interface between the first and second adapter elements when the elements are coupled; and
    (b) placing the adapter component in an acetabular cup;
    (c) inserting a liner into the adapter component and cup;
    (d) rotating the liner as required to obtain optimal positioning;
    (e) seating the liner;
    (f) selecting and assembling an appropriately sized implant stem head and femoral stem component;
    (g) inserting the implant stem head into the cavity of the liner;
    (h) rotating the femoral component to check mobility.

* * * * *